United States Patent [19]

Bonjouklian et al.

[11] Patent Number: 4,874,782

[45] Date of Patent: Oct. 17, 1989

[54] FURANONE DERIVATIVES

[75] Inventors: Rosanne Bonjouklian, Indianapolis, Ind.; Christopher J. M. Meade, Lightwater, England; Edward D. Mihelich; Michael L. Phillips, both of Indianapolis, Ind.

[73] Assignee: Eli Lilly and Company, Indianapolis, Ind.

[21] Appl. No.: 66,907

[22] Filed: Jun. 26, 1987

Related U.S. Application Data

[63] Continuation of Ser. No. 750,801, Jul. 1, 1985, abandoned.

[51] Int. Cl.$^4$ .................. C07D 307/60; A61K 31/365
[52] U.S. Cl. ..................................... 514/473; 549/313
[58] Field of Search ......................... 549/313; 514/473

[56] References Cited

U.S. PATENT DOCUMENTS 4,447,445 5/1984 Jacobs et al. ...................... 424/279
4,616,089 10/1986 Jacobs et al. ...................... 549/323

OTHER PUBLICATIONS

Derwent 87083 E/41, Abstracting J5 7144-245.
Kikuchi et al., Chem. Parm. Bull., 31 (4), 1172-1176, (1983).
S. Katsumara et al., *Heterocycles*, vol. 10, (1978), pp. 87-91.
B. Sullivan et al., *Tetrahedron Letters*, vol. 23, (9), (1982), pp. 907-910.
J. J. Bourguignon et al., J. Org. Che., (1981), vol. 46, pp. 4889-4894.
Derwent 89586 E/42, Abstracting J5, 7149-283.

*Primary Examiner*—Glennon H. Hollrah
*Assistant Examiner*—Mark W. Russell
*Attorney, Agent, or Firm*—Joseph A. Jones; Leroy Whitaker

[57] ABSTRACT

This invention provides certain furanone derivatives, their pharmaceutical formulations, and their use in a method for treating inflammation, asthma, or allergies.

13 Claims, No Drawings

FURANONE DERIVATIVES

This application is a continuation of application Ser. No. 750,801, filed July 1, 1985 now abandoned.

BACKGROUND OF THE INVENTION

Phospholipase $A_2$ ($PLA_2$) is a calcium-dependent enzyme which cleaves the R-2 acyl group of phospholipids. In mammalian tissues, this cleavage primarily yields free arachidonic acid which can then be converted by the cyclooxygenase system to prostaglandins and thromboxanes. Alternatively, arachidonic acid can be converted into leukotrienes via the lipoxygenase pathway. See generally G. Weissman, *Cellular Immunology*, 82, 117 (1983). See also E. Israel and J. M. Drazen, "Leukotrienes and Asthma: A Basic Review" in *Current Concepts in Allergy and Clinical Immunology*, Vol XIV, No 3. pp. 11–16 (1983).

Many anti-inflammatory agents, such as aspirin, indomethacin, and ibuprofen, block the formation of prostaglandins by inhibiting the cyclooxygenase pathway. Similarly, inhibition of the lipoxygenase pathway, and therefore the formation of leukotrienes, has also been shown to produce an anti-inflammatory effect. An inhibitor of $PLA_2$, which would prevent the release of arachidonic acid, would effectively block both pathways and should be an effective anti-inflammatory agent by inhibiting the production of mediators from both pathways.

It is the purpose of this invention to provide certain furanone derivatives which are useful as anti-inflammatory and anti-allergy agents by virtue of their ability to inhibit the enzyme $PLA_2$.

SUMMARY OF THE INVENTION

This invention provides compounds of the formula

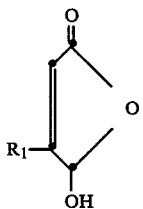

I wherein R is a $C_8$–$C_{24}$ straight or branched hydrocarbyl group optionally containing a total of 1–6 double and/or triple bonds and optionally containing an aldehyde or hydroxymethyl group, or R-alk- where alk is a $C_2$–$C_{12}$ straight or branched hydrocarbyl group optionally containing 1 or 2 double or triple bonds and R is napthalenyloxy or benzylphenoxy.

In addition to the compounds as defined by the above formula, this invention also provides a method of treating inflammation, asthma, allergies, and any other related disease caused by an excess of prostaglandins, thromboxanes, or leukotrienes, in a mammal which comprises administering to said mammal an effective amount of a compound of this invention.

According to a further aspect of the present invention, there are provided pharmaceutical formulations which comprise as active ingredient a furanone of the above formula in association with a pharmaceutically acceptable carrier, diluent, or excipient therefor.

DETAILED DESCRIPTION AND PREFERRED EMBODIMENTS

A preferred group of compounds are those of the above formula wherein R is a hydrocarbyl group of 10 to 20, especially 12–16, carbon atoms. The hydrocarbyl group can be straight or branched and preferably contains 2–4 double bonds. An especially preferred definition of R is

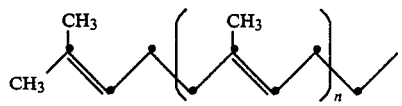

where n is 1 or 2. Optionally, the methyl group attached to the ethylene carbon atom closest to the furanone ring may be replaced with a carboxaldehyde or hydroxymethyl group.

"Napthalenyloxy" refers to 1- and preferably 2-napthalenyloxy. "Benzylphenoxy" refers to 3-, 4-, and preferably 2-benzylphenoxy. "Alk" is a divalent organic radical derived from a $C_2$–$C_{12}$ hydrocarbon and is preferably di-, tri-, or tetra-methylene.

The compounds of the present invention can be prepared by any of several methods known to those skilled in the art. A reaction sequence which is particularly useful for preparing the fatty acid derivatives of this invention is summarized in Scheme I.

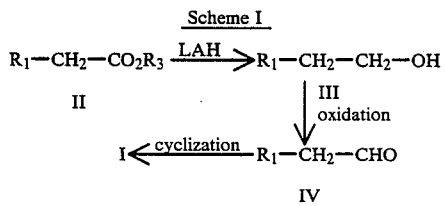

where $R_3$ is methyl or ethyl.

According to Scheme I, the methyl or ethyl ester II is transformed into the corresponding alcohol III upon treatment with a reducing agent, such as lithium aluminum hydride, in a non-reactive solvent such as tetrahydrofuran or diethyl ether, preferably at temperatures from about −20° to 20° C. In general, a slight molar excess of ester II is used to prevent reduction of any unsaturated bonds.

The resulting alcohol III is then oxidized to the corresponding aldehyde IV employing a Swern oxidation. This procedure is generally carried out at temperatures from about −60° to 0° C. and involves the use of approximately 1 molar equivalent of oxalyl chloride, approximately 2 molar equivalents of dimethylsulfoxide, and 3–8 molar equivalents of triethylamine, usually in the presence of a non-reactive solvent such as dichloromethane.

Aldehyde IV can then be converted into the desired furanone I following the procedure reported by Bourguignon, et al., *J. Org. Chem.*, 46, 4889 (1981). In general, the aldehyde is allowed to reflux with approximately molar equivalents of glyoxylic acid and morpholine hydrochloride in a mixture of dioxane and water under an inert atmosphere. The reaction is generally complete within about 24 hours when the reaction is heated at the reflux temperature of the mixture.

An alternate procedure especially useful in the preparation of the naphalenyloxy compounds of this invention is summarized in Scheme II. The benzylphenoxy derivatives may be prepared by the same method beginning with the appropriate benzylphenol.

tion with a hindered reducing agent followed by an acidic work-up. The preferred reducing agent is diisobutyl aluminum hydride. The reaction is generally carried out under an inert atmosphere at temperatures from about $-20°$ to $20°$ C. in the presence of a non-reactive

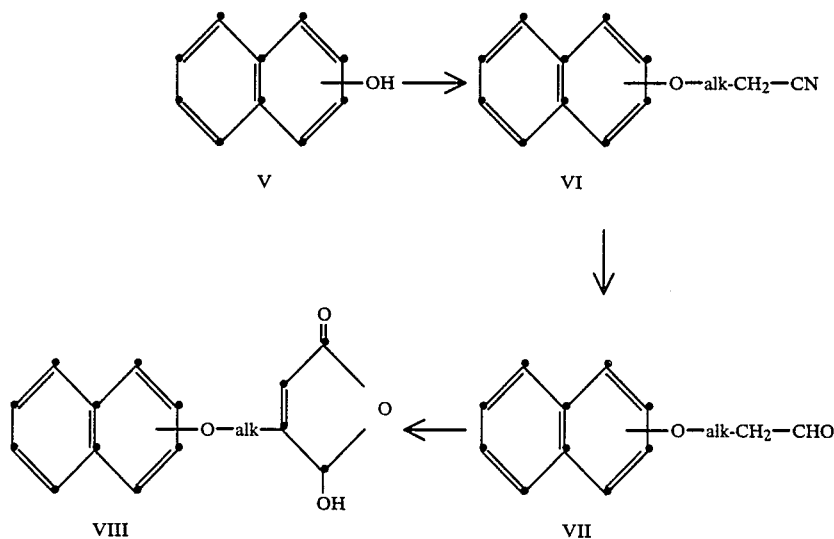

Scheme II

Naphthol V is alkylated with X—alk—CH$_2$—CN, where X is chloro or bromo, to provide the corresponding nitrile derivative VI. Standard alkylation techniques are employed. The preferred conditions consist of the reaction of naphthol V with a strong base such as sodium hydride, in a non-reactive solvent such as dimethylformamide. The reaction is generally carried out at temperatures from about 20°–100° C. and is preferably carried out in the presence of a catalytic amount of an alkali metal iodide, such as potassium or sodium iodide.

The nitrile intermediate VI may be converted directly into the aldehyde intermediate VII upon reduction with a hindered reducing agent followed by an acidic work-up. The preferred reducing agent is diisobutyl aluminum hydride. The reaction is generally carried out under an inert atmosphere at temperatures from about $-20°$ to $20°$ C. in the presence of a non-reactive solvent such as tetrahydrofuran. Generally, 4 molar equivalents of the reducing agent are employed. The acidic hydrolysis is accomplished simply by adding an acid, such as a mineral acid, for example hydrochloric acid, to the reaction mixture. The resulting aldehyde VII can then be converted into the final product VIII following the same procedure as described in Scheme I for converting intermediate IV into product I.

Another method of preparing the compounds of formula I, and especially useful for preparing compounds wherein R$_1$ is a terpene derivative, is depicted in Scheme III as applied to a terpene side chain.

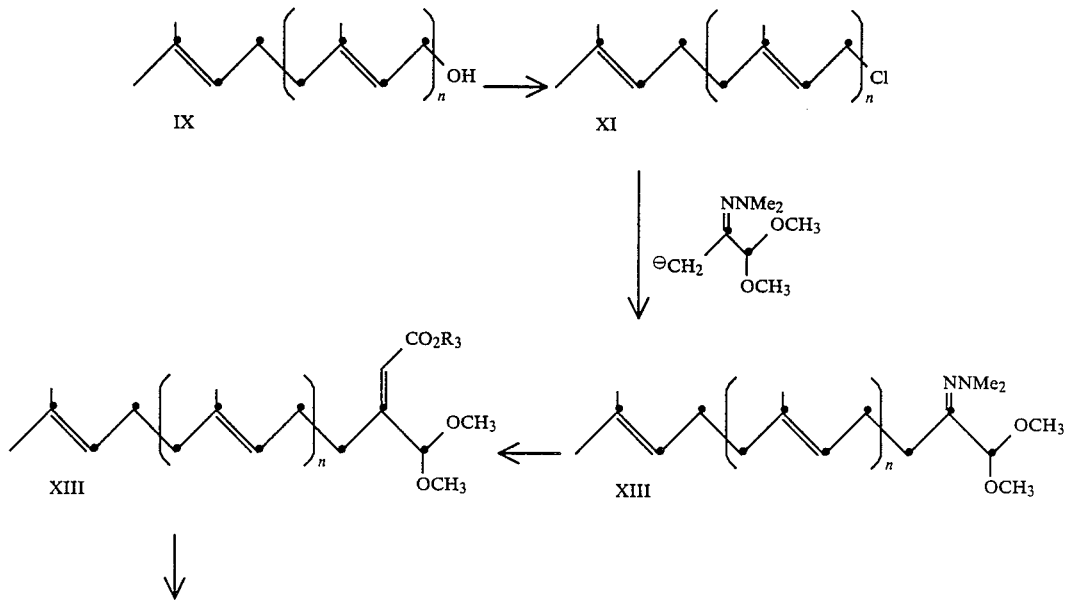

Scheme III

-continued
Scheme III

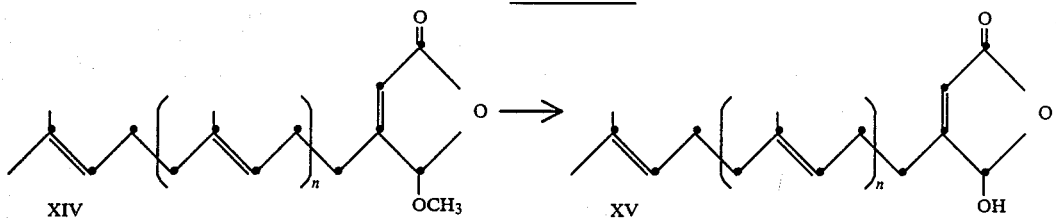

wherein n is 1 or 2. An alcohol IX is transformed into the corresponding chloro derivative XI by methods known in the art. Especially useful for this transformation when a terpene is involved is 2, 4, 6-collidine, lithium chloride, dimethylformamide, and methanesulfonyl chloride following the general procedure of Collington et al., *J. Org. Chem.*, 36 (20), 3044 (1971). The reaction of the chloro intermediate XI to the dimethylacetal intermediate XII is accomplished by reacting the anion of the dimethyl hydrazone derivative of pyruvic aldehyde dimethylacetal following the general procedure of Cuvigny et al., *Synthesis*, 198 (1977). The required dimethyl hydrazone of pyruvic aldehyde dimethylacetal is prepared following the procedure of Newkome et al., *J. Org. Chem.*, 31, 677 (1966) and Smith et al., *J. Org. Chem.*, 22, 358 (1957) and as described in the examples which follow. The resulting hydrazone XII is first hydrolyzed with acid to provide the corresponding keto acetal and then treated with the lithium derivative of an alkyl trimethylsilylacetate following the procedure of Hartzell et al., *Tetrahedron Letters*, 15, 1403 (1974) and Rathke et al., *Syn. Comm.*, 3 (1), 67 (1973). Treatment of intermediate XIII with acidic silica gel (Larcheveque et al., *Tetrahedron Letters*, 22 (17), 1595 (1981)) provides the methoxy analog of XIV which is converted to the desired product XV upon treatment with approximately 1 molar equivalent of 0.1N sodium hydroxide or a related base.

A similar sequence can be employed to prepare terpene derivatives having a carboxaldehyde substituent as summarized in Scheme IV.

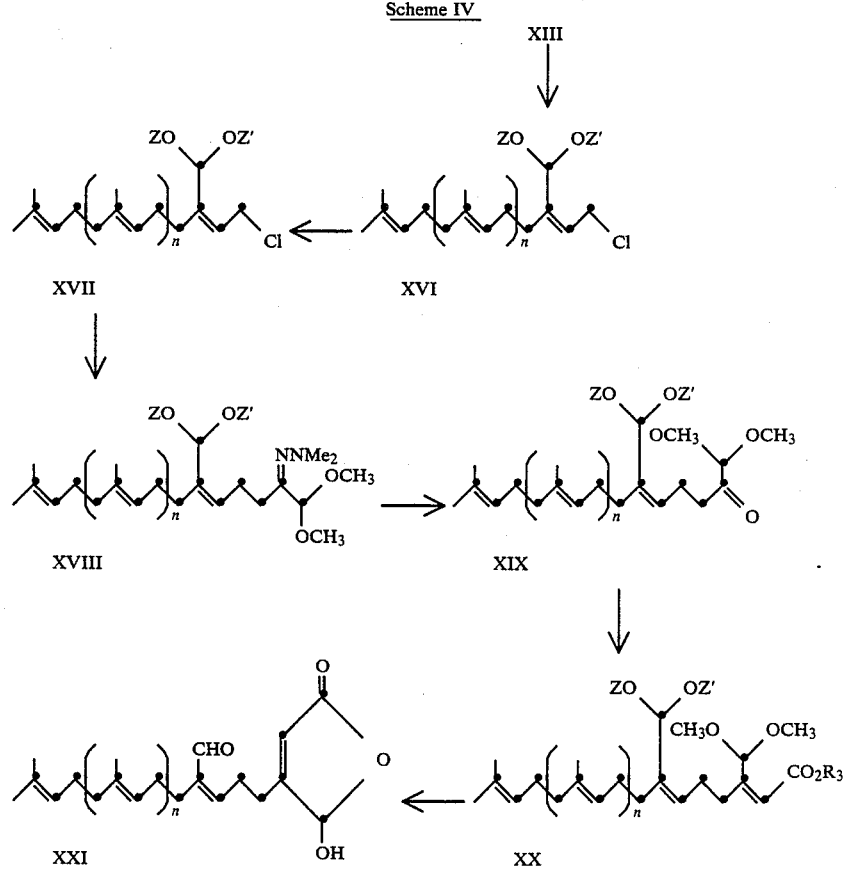

where Z and Z' are independently methyl or ethyl, or when taken together Z and Z' are di-, tri-, or tetramethylene. According to Scheme IV, intermediate XIII is treated with a reducing agent such a lithium aluminum hydride to give the corresponding alcohol XVI. Following the general sequence of Scheme III above, the alcohol is transformed into the chloro derivative XVII which is, in turn, transformed into the hydrazone intermediate XVIII. Intermediate XVIII is converted into the final product XXI by hydrolysis to the diacetal intermediate XIX, transformation to ester XX, and acidic hydrolysis to prepare the desired final compound XXI and the undesired 2-methoxy analogue which can be used as an intermediate in preparing the hydroxymethyl compounds of this invention as discussed below.

Compounds of the type represented by Formula XXI can also be used as intermediates to the corresponding hydroxymethyl analogs. Standard reductive techniques can be employed, such as sodium borohydride treatment in a non-reactive solvent such as methanol. Alternatively, this reaction is preferably performed on the 2-methoxy derivative formed as a by-product when transforming XX into XXI as taught above. After reduction of the aldehyde, the methoxy group is converted to the desired hydroxy functionality upon mild basic hydrolysis as previously described.

Intermediates II, III, IV, V, and IX and other required reagents are commercially available, are known in the literature, or can be prepared by methods known in the literature or by the methods described in the following examples.

The hydroxy substituent of the furanone ring of formula I can exist in either of two stereoisomeric forms. In addition, the R substituents may include double bonds in either the cis or trans form. This invention is not limited to any particular isomer but includes all possible individual isomers and racemates of the compounds of formula I.

The following examples further illustrate the preparation of the compounds of this invention. The examples are illustrative only and are not intended to limit the scope of the invention in any way.

EXAMPLE 1

(Z,Z)-4-(7,10-hexadecadienyl)-5-hydroxy-2(5H)-furanone

A. Preparation of linoleyl alcohol.

A solution of 20.0 g of methyl linoleate in 20 ml of diethyl ether was added to a suspension of 1.8 g of lithium aluminum hydride in 150 ml of diethyl ether at approximately 0° C. under an argon atmosphere. The mixture was stirred for approximately 2 hours at 0° C. The reaction was quenched by the slow addition of 1.8 ml of water, followed by 1.8 ml of 15% sodium hydroxide and 5.4 ml of water. The mixture was filtered and the filtrate was evaporated to dryness. The resulting oil was dissolved in diethyl ether, washed with water, dried over magnesium sulfate, filtered, and evaporated to provide 17.7 g of linoleyl alcohol.

B. Preparation of linoleyl aldehyde.

A solution of 20.23 ml of dimethylsulfoxide in 47 ml of methylene chloride was added dropwise to a stirred solution of 12.3 ml of oxalyl chloride in 230 ml of methylene chloride under an argon atmosphere at approximately −60° C. After stirring the mixture for 5 minutes, a solution of 25 g of linoleyl alcohol in 50 ml of methylene chloride was added while maintaining the temperature below −50° C. The reaction was stirred for 20 minutes at −50° C. and slowly allowed to warm to −20° C. The reaction was quenched by the addition of 61 ml of triethylamine. After stirring at −20° C. for 5 minutes, the mixture was warmed to room temperature and evaporated to dryness. The residue was dissolved in diethyl ether, washed twice with water and once with a saturated sodium chloride solution, dried over magnesium sulfate, and concentrated in vacuo. The resulting oil was purified by flash chromatography using 10:1 hexane/diethyl ether to provide 17.1 g of linoleyl aldehyde.

C. Preparation of (Z,Z)-4-(7,10-hexadecadienyl)-5-hydroxy-2(5H)-furanone.

Under a nitrogen atmosphere, 2.33 g of glyoxylic acid hydrate, 3.44 g of morpholine hydrochloride, and 10.1 ml of dioxane were mixed with rapid stirring in a 50 ml round bottom flask. Water was added in a dropwise fashion in an amount sufficient to obtain a homogenous solution. Six and seven-tenths grams of linoleyl aldehyde were added. The mixture was stirred vigorously for 1 hour and then heated at reflux for 24 hours. The reaction mixture was evaporated in vacuo. The resulting oil was dissolved in diethyl ether, washed with water, dried over magnesium sulfate, filtered, and evaporated. The resulting crude oil was purified by medium pressure chromatography over silica gel eluting with 3:1 hexane/ethyl acetate. The appropriate fractions were combined and evaporated to provide 4.0 g of the desired title product as a colorless oil.

Analysis for $C_{20}H_{32}O_3$: Calculated: C, 75.19; H, 9.78; Found: C, 75.01; H, 10.01.

EXAMPLES 2–11

The following compounds were prepared according to the procedures of Example 1 from the appropriate intermediates. Yields are expressed as the molar yields from the respective intermediates.

2. Z,Z,Z)-4-(7,10,13-hexadecatrienyl)-5-hydroxy-2(5H)-furanone, oil, 34.9% yield from the alcohol intermediate. The IR, proton NMR and $^{13}C$ NMR spectra were consistent with the structure of the product.

3. (Z,Z,Z,Z)-5-hydroxy-4-(3,6,9,12-octadecatetraenyl)-2(5H)-furanone, oil, 22.8% yield from the methyl ester intermediate. The IR, proton NMR, and $^{13}C$ NMR spectra were consistent with the structure of the product.

4. (E)-4-(7-hexadecenyl)-5-hydroxy-2(5H)furanone, oil, 32.0% yield from the methyl ester intermediate. The IR, proton NMR, and $^{13}C$ NMR spectra were consistent with the structure of the desired product.

Analysis for $C_{20}H_{34}O_3$: Calculated: C, 74.49; H, 10.63; Found: C, 73.88; H, 9.87.

5. (Z,Z,Z)-4-(4,7,10-hexadecatrienyl)-5-hydroxy-2(5H)-furanone, oil, 51.2% yield from the methyl ester intermediate. The IR, proton NMR, and $^{13}C$ NMR spectra were consistent with the structure of the product.

Analysis for $C_{20}H_{30}O_3$: Calculated: C, 75.43; H, 7.50; Found: C, 75.17; H, 7.31.

6. 4-Hexadecyl-5-hydroxy-2(5H)-furanone, oil, 18.6% yield from the aldehyde intermediate. The IR and proton NMR spectra were consistent with the structure of the product.

Analysis for $C_{20}H_{36}O_3$: Calculated: C, 74.03; H, 11.18; Found: C, 73.80; H, 10.87.

7. 5-Hydroxy-4-(8-nonenyl)-2(5H)-furanone, oil, 52.5% yield from the aldehyde intermediate. The IR, proton NMR, and $^{13}C$ NMR spectra were consistent with the structure of the product.

Analysis for $C_{13}H_{20}O_3$: Calculated: C, 69.61; H, 8.99; Found: C, 69.37; H, 8.76.

8. (Z)-4-(9-hexadecenyl)-5-hydroxy-2(5H)furanone, oil, 74.9% yield from the alcohol. The IR, proton NMR, and $^{13}C$ NMR spectra were consistent with the structure of the product.

Analysis for $C_{20}H_{34}O_3$: Calculated: C, 74.49; H, 10.63; Found: C, 74.24; H, 10.62.

9. (Z,Z,Z,Z,Z,Z)-4-(2,5,8,11,14,17-eicosahexaenyl)-5-hydroxy-2(5H)-furanone, oil, 46.4% yield from the methyl ester intermediate. The IR, proton NMR, and $^{13}C$ NMR spectra were consistent with the structure of the product.

10. (Z)-4-(11-eicosenyl)-5-hydroxy-2(5H)furanone, oil, 56.1% yield from the methyl ester intermediate. The IR, proton NMR, and $^{13}C$ NMR spectra were consistent with the structure of the product.

Analysis for $C_{24}H_{42}O_3$: Calculated: C, 76.14; H, 11.18; O, 12.68; Found: C, 76.43; H, 11.12; O, 12.92.

11. (Z)-4-(7-hexadecenyl)-5-hydroxy-2(5H)furanone, oil, 47.2% yield from the aldehyde intermediate. The proton NMR and mass spectra were consistent with the structure of the product.

EXAMPLE 12

5-Hydroxy-4-[4-(2-naphthalenyloxy)butyl]-2(5H)furanone

A. Preparation 6-(2-naphthalenyloxy)hexane nitrile.

To a solution of 10.0 g of 2-naphthol in 185 ml of dimethylformamide were added 2.91 g of 60% sodium hydride in oil in small portions. After hydrogen evolution had ceased, 7.52 ml of 6-bromocapronitrile were added and the reaction was heated to 60° C. for approximately 18 hours. A catalytic amount of sodium iodide was added and the reaction was stirred for approximately 24 hours at 60° C. After heating an additional 24 hours at 80° C., the reaction mixture was cooled and treated with 2 ml of water. The solution was concentrated in vacuo. The residue was dissolved in diethyl ether, washed several times with water, dried over magnesium sulfate, and evaporated to provide a crude oil. Crystallization from diethyl ether/pentane provided 7.5 g of the desired subtitle intermediate, m.p. 55°–56° C.

B. Preparation of 6-(2-naphthalenyloxy)hexanal.

Four grams of 6-(2-naphthalenyloxy)hexane nitrile were dissolved in 170 ml of tetrahydrofuran. The solution was cooled to approximately 0° C. and 57.6 ml of a 1.2M solution of diisobutyl aluminum hydride in hexane were added in a dropwise fashion with an argon blanket over the reaction mixture. The reaction was stirred for 6 hours at 0° C. at which time 33.5 ml of 2M hydrochloric acid were added. The reaction mixture was concentrated in vacuo and dissolved in 1:1 diethyl ether/ethyl acetate. The organic layer was separated and washed 3 times with water, dried over magnesium sulfate, filtered, and evaporated to provide 3.3 g of the desired subtitle intermediate as a yellow oil which was used in the subsequent reaction without further purification.

C. Preparation of 5-hydroxy-4-4-(2-naphthalenyloxy)butyl]-2(5H)-furanone.

Following the procedure of Example 1C, 3.3 g of 6-(2-naphthalenyloxy)hexanal were transformed into 1.84 g of the title product, m.p. 105°–107° C. The IR, proton NMR, and $^{13}C$ NMR spectra were consistent with the structure of the product.

Analysis for $C_{18}H_{18}O_4$: Calculated C, 72.47; H, 6.08; Found: C, 72.47; H, 6.08.

EXAMPLE 13

5-Hydroxy-4-(4,8,12-trimethyl-3,7,11-tri-decatrienyl)-2(5H)-furanone

A. Preparation of farnesyl chloride.

A stirred mixture of 2.0 g of farnesol and 1.31 ml of 2,4,6-collidine under an argon atmosphere was treated with 381 mg of lithium chloride dissolved in approximately 5 ml of dimethylformamide. The solution was cooled to approximately 0° C. at which time a suspension formed. The suspension was treated with 0.766 ml of methanesulfonyl chloride. After stirring for 3 hours, the suspension was poured into ice water and extracted with 1:1 diethyl ether/pentane. The combined organic extracts were washed 4 times with a concentrated solution of copper nitrate until no further intensification of the blue-colored copper solution occurred indicating the complete removal of collidine. The organic layer was dried over magnesium sulfate, filtered and evaporated to provide 2.0 g of the desired subtitle intermediate as a colorless oil which was used without further purification.

B. Preparation of farnesyl keto-acetal.

A solution of 1.29 ml of diisopropylamine in 50 ml of tetrahydrofuran was cooled to 0° C. by means of external ice bath. An argon atmosphere was introduced followed by the addition of 5.7 ml of a 1.6M solution of n-butyllithium in hexane. After stirring for 15 minutes, a solution of 1.31 g of pyruvaldehyde dimethyl hydrazone dimethyl acetal in 5 ml of tetrahydrofuran was added. After stirring for 30 minutes, 2.0 g of farnesyl chloride in 5 ml of tetrahydrofuran were added to the reaction mixture. The reaction mixture was kept at approximately −10° C. for three days. Three milliliters of 1:1 water/tetrahydrofuran were added to the solution and the reaction was concentrated in vacuo. The residue was dissolved in diethyl ether, washed with water, dried over magnesium sulfate, filtered, and evaporated to provide 2.6 g of a crude yellow oil. The oil was dissolved in 20 ml of tetrahydrofuran and treated with 13 ml of 2N hydrochloric acid. An additional 175 ml of diethyl ether were added and the layers were separated. The organic layer was washed sequentially with water, a 5% sodium bicarbonate solution, and water, dried over magnesium sulfate, filtered, and evaporated in vacuo. The resulting oil was purified by medium pressure liquid chromatography over silica gel eluting with 6:1 hexane/diethyl ether providing 1.4 g of the desired subtitle intermediate. Proton NMR spectroscopy confirmed the structure of the desired intermediate.

C. Preparation of tert-butyl 3-dimethoxymethyl-7,11,15-trimethyl-2,6,10,14-hexadecatetraenoate.

A solution of 0.47 ml of diisopropylamine in 25 ml of tetrahydrofuran was cooled to 0° C. Under an argon atmosphere, 2.0 ml of a 1.67M solution of n-butyllithium in hexane were added. The reaction mixture was stirred for 15 minutes and then cooled to −78° C. by means of an external dry ice/acetone bath. A solution of 0.57 g of tert-butyl trimethylsilylacetate in 5 ml of tetrahydrofuran was added in a dropwise fashion and the reaction was stirred for 13 minutes. A solution of 1.0 g of farnesyl keto-acetal in 5 ml of tetrahydrofuran was added and the reaction was stirred while allowing the temperature to rise to ambient temperature. The solution was cooled once again to −78° C. and 2 ml of a saturated ammonium chloride solution were added. The mixture was evaporated in vacuo and the residue was diluted with diethyl ether, washed twice with water, dried over magnesium sulfate, filtered, and evaporated to provide 1.27 g of the desired subtitle intermediate as a 1:3 mixture of E/Z isomers as indicated by proton NMR and also by analytical HPLC.

D. Preparation of 5-methoxy-4-(4,8,12-trimethyl-3,7,11-tridecatrienyl)-2(5H)-furanone.

A solution of 1.28 g of tert-butyl 3-dimethoxymethyl-7,11,15-trimethyl-2,6,10,14-hexadecatetraenoate in 30 ml of methylene chloride was treated with 7.4 g of acidic silica gel (prepared from drying a slurry of 50 g of Woelm silica gel (100–200 μm) with 14 g of 15% sulfuric acid overnight at 40° C). The reaction was stirred under an argon atmosphere for approximately 18 hours. The reaction mixture was filtered and the silica gel was washed several times with methylene chloride. The combined methylene chloride solutions were evaporated to dryness. The resulting oil was dissolved in ether, washed with water, dried over magnesium sulfate, filtered and evaporated. The resulting oil was chromatographed by medium pressure liquid chromatography over silica gel eluting with 4:1 hexane/ethyl acetate to provide 580 mg of the desired subtitle intermediate as a colorless oil. The compound was a mixture of all eight isomers of the position 3 and 7 double bonds and isomeric methoxy substituent.

E. Preparation of 5-hydroxy-4-(4,8,12-trimethyl-3,7,11-tridecatrienyl)-2(5H)-furanone.

Three hundred and ten milligrams of the intermediate from Example 13D were dissolved in 200 ml of tetrahydrofuran. The solution was treated with 9.9 ml of 0.1N sodium hydroxide and stirred for 3 days. The reaction was cooled to 0° C. and brought to pH 4 with the addition of 0.1N hydrochloric acid. The mixture was extracted with diethyl ether. The organic extract was dried over magnesium sulfate, filtered, and evaporated to provide an oil. Purification by medium pressure liquid chromatography over silica gel eluting with 3:1 hexane/ethyl acetate provided 180 mg of the desired title product as an oil. The product was a mixture of eight isomers consisting of the double bond isomers at positions 3 and 7 of the side chain as well as the isomeric hydroxy substituent. The infrared, proton NMR, and $^{13}$C NMR spectra were consistent with the structure of the desired product.

Analysis for $C_{20}H_{30}O_3$: Calculated: C, 75.43; H, 9.50; Found: C, 74.03; H, 10.08.

EXAMPLE 14

(E,E)-4-(4,8-dimethyl-3,7-nonadienyl)-5-hydroxy-2(5H)-furanone

The title product was prepared in an overall yield of 17.9% from geraniol following the procedure of Example 13. The IR, proton NMR, and $^{13}$C NMR spectra were consistent with the structure of the desired product.

Analysis for $C_{15}H_{22}O_3$: Calculated: C, 71.97; H, 8.86; O, 19.17; Found: C, 71.76; H, 8.66; O, 19.37.

EXAMPLE 15

2-[3-(2,5-dihydro-2-hydroxy-5-oxo-3-furanyl)-propylidene]6,10-dimethyl-5,9-undecadienal A. Preparation of tert-butyl 3-dimethoxymethyl-7,11-dimethyl-2,6,10-undecatrienoate.

A solution of 1.16 ml of diisopropylamine in 50 ml of tetrahydrofuran was stirred for 30 minutes at 0° C. Under an argon atmosphere, 5.16 ml of a 1.68M solution of n-butyllithium in hexane were added. After stirring for 15 minutes, the reaction mixture was cooled to −78° C. and stirred for 30 minutes. Tert-butyl trimethylsilylacetate (1.56 g) was added to the reaction mixture. After stirring for 1 hour, a solution of 2.0 g of the geranyl keto-acetal intermediate formed in Example 14, prepared from geraniol following the general procedures of Examples 13A and 13B, in 5 ml of tetrahydrofuran was added to the solution. The reaction mixture was stirred for 15 minutes and allowed to warm to room temperature. The solution was again cooled to −78° C. and hydrolyzed by the addition of 2 ml of a saturated ammonium chloride solution. The reaction mixture was evaporated in vacuo, dissolved in diethyl ether, washed twice with water and once with a saturated sodium chloride solution, dried over magnesium sulfate, filtered and evaporated to provide an oil. Purification by medium pressure liquid chromatography provided 2.49 g of the desired subtitle intermediate as a 1:4 mixture of the E/Z isomers as determined by proton NMR.

B. Preparation of 3-dimethoxymethyl-7,11-dimethyl-2,6,10-undecatrien-1-ol.

One gram of the intermediate described in Example 15A was added to a suspension of 82.3 mg of lithium aluminum hydride in 25 ml of diethyl ether under an argon atmosphere at 0° C. After 1 hour, 0.08 ml of water were added followed by the addition of 0.08 ml of 15% sodium hydroxide and 0.24 ml of water. The mixture was filtered and the filtrate was extracted several times with diethyl ether. The organic extracts were combined and washed with water and a saturated sodium chloride solution, dried over magnesium sulfate, filtered and concentrated in vacuo to provide 881 mg of the desired subtitle intermediate as a colorless oil.

C. Preparation of 3-dimethoxymethyl-7,11-dimethyl-2,6,10-undecatrienyl chloride.

Following the general procedure of Example 13A, 430 mg of the alcohol from Example 15B were transformed into 458 mg of the subtitle intermediate which was used immediately for the subsequent reaction.

D. Preparation of 1,1-dimethoxy-6-dimethoxymethyl-10,14-dimethyl-5,9,13-pentadecatrien-2-one dimethylhydrazone.

Following the general procedure of Example 13B, 3.77 g of pyruvaldehyde dimethyl hydrazone dimethyl acetal and 276 mg of the chloride from Example 15C. were reacted to provide 5.18 g of crude product which was purified by medium pressure liquid chromatography to give 1.19 g of the desired subtitle intermediate.

E. Preparation of 1,1-dimethoxy-6-dimethoxymethyl-10,14-dimethyl-5,9,13-pentadecatriene-2-one.

Five grams of Woelm silica (100–200 μm, active) were slurried with 30 ml of methylene chloride under an argon atmosphere. Five-tenths of a milliliter of water were added. After additional stirring, 1.2 g of hydrazone from Example 15D were added and the reaction was stirred for 2 hours. An additional 0.1 ml of water was added and the reaction was stirred an additional hour. One gram of silica gel was added and the reaction was stirred an additional hour. An additional gram of gel and an additional 0.1 ml of water were added and the reaction was stirred an additional 2 hours. The reaction was filtered and the silica gel was washed with acetone. The combined organic filtrates were concentrated to dryness, dissolved in diethyl ether, washed with water and a saturated sodium chloride solution, dried over magnesium sulfate and concentrated to dryness to provide 829 mg of the subtitle intermediate as an oil which was used without further purification.

F. Preparation of tert-butyl 3,7-dimethoxymethyl-11,15-dimethyl-2,6,10,14-hexadecatetraenoate.

Following the general procedure of Example 13C, 829 mg of ketone from Example 15E and 551 mg of tertbutyl trimethylsilylacetate were reacted to provide 720 mg of the desired subtitle intermediate.

G. Preparation of 2-[3-(2,5-dihydro-2-hydroxy5-oxo-3-furanyl)propylidene]-6,10-dimethyl-5,9-undecadienal.

Following the general procedure of Example 13D, 720 mg of ester from Example 15F were treated with 3.9 g of 10% sulfuric acid/silica gel in 16 ml of methylene chloride for 6 hours. After the standard work-up and purification by chromatography, 62.0 mg of the desired title product were recovered as well as 166 mg of the 2-methoxy intermediate. The IR, proton NMR, $^{13}C$ NMR, and mass spectra were consistent with the structure of the desired product.

Analysis for $C_{20}H_{28}O_4$: Calculated: C, 72.26; H, 8.49; Found: C, 72.14; H, 8.62.

EXAMPLES 16–18

The following compounds were prepared from the appropriate naphthol or benzylphenol and the corresponding omega-haloalkyl nitrile according to the procedures of Example 12.

16. 5-Hydroxy-4-[5-(2-naphthalenyloxy)pentyl]2(5H)-furanone, m.p. 89°–94° C., 11.8% yield from 2-naphthol. The IR, proton NMR, and $^{13}C$ NMR spectra were consistent with the structure of the desired product.

Analysis for $C_{19}H_{20}O_4$: Calculated: C, 73.06; H, 6.45; Found: C, 73.21; H, 6.48.

17. 5-Hydroxy-4-[4-(2-benzylphenoxy)butyl]- 2(5H)-furanone, m.p. 72–75° C, 24.4% yield from 2-hydroxydiphenyl methane. The IR, proton NMR, and $^{13}C$ NMR spectra were consistent with the structure of the desired product.

Analysis for $C_{21}H_{22}O_4$: Calculated: C, 74.54; H, 6.55; Found: C, 74.31; H, 6.35. 18. 5-Hydroxy-4-[5-(2-benzylphenoxy)pentyl]2(5H)-furanone, m.p. 98°–99° C., 33.2% yield from 2-hydroxydiphenyl methane. The IR, proton NMR, $^{13}C$ NMR, and mass spectra were consistent with the structure of the desired product.

EXAMPLE 19

5-Hydroxy-4-[4-(hydroxymethyl)-8,12-dimethyl3,7,11-tridecatrienyl]-2(5H)-furanone A solution of 100 mg of 2-[3-(2,5-dihydro-2-methoxy-5-oxo-3-furanyl)propylidene]-6,10-dimethyl-5,9-undecadienal (Example 15G) and 10.9 mg of sodium borohydride in 30 ml of dry methanol under an argon atmosphere was stirred for four hours at room temperature followed by four hours of stirring at 35° C. The reaction was quenched by the slow addition of water and the mixture was extracted with ether. The organic layer was washed with water and a saturated sodium chloride solution, dried over magnesium sulfate and evaporated in vacuo. The residue was dissolved in 3 ml of tetrahydrofuran and 0.34 ml of 0.1N sodium hydroxide at room temperature and under argon. The solution was brought to reflux for two hours, cooled, and adjusted to pH 4 with the slow addition of 0.1N hydrochloric acid. Extraction with ether provided an organic solution which was washed with 0.01N hydrochloric acid and a saturated sodium chloride solution, dried over magnesium sulfate, and concentrated in vacuo. The resulting oil was purified by medium pressure liquid chromatography over silica gel eluting with 1:2 hexane/ethyl acetate to afford 56.8 mg of the title product as an oil. Proton NMR, $^{13}C$ NMR, and mass spectra were consistent with the desired structure.

EXAMPLE 20

4-Heptadecyl-5-hydroxy-2(5H)-furanone

The title compound was prepared in 54% yield from the corresponding 5-methoxy derivative upon heating with concentrated hydrochloric acid. Proton NMR and mass spectra were consistent with the structure of the desired product.

EXAMPLE 21

(Z)-4-(11-hexadecenyl)-5-hydroxy-2(5H)-furanone

Following the procedure of Example 1, the title compound was prepared in 69.4% yield from the corresponding aldehyde intermediate. The infrared, proton NMR, and mass spectra were consistent with the structure of the desired product.

Analysis for $C_{20}H_{34}O_3$: Calculated: C, 74.49; H, 10.63; Found: C, 74.28; H, 10.44.

The compounds of formula I inhibit the enzymes phospholipase $A_2$, 5-lipoxygenase, and fatty acid cyclooxygenase. The compounds are therefore useful as anti-inflammatory, anti-allergy and anti-asthma agents. These pharmacodynamic effects of the compounds of this invention were demonstrated in the following test systems.

5-Lipoxygenase (5-LPO) Assay

Ten milliliters of a 2% casein solution were injected intraperitoneally to guinea pigs weighing 250–300 gm. After 16–18 hours, the guinea pigs were killed by suffocation in a carbon dioxide chamber. The peritoneal cavity was infused with 70 ml of saline and 40–50 ml of the fluid were recovered from the cavity. After centrifugation, cell pellets were washed twice in Hank's balanced salt solution (HBSS) without calcium ion.

The cells were then suspended in 5 ml of sodium phosphate buffer, pH 7.1 containing 1 mM EDTA, and 0.1% gelatin. About $20-30 \times 10^7$ cells were obtained from one guinea pig. Analysis for the cell composition indicated that more than 95 percent of the cells were polymorphonuclear leukocyte (PMNL).

The PMNL suspension was disrupted by five ½-second pulse sonication at the setting of 3 in a Branson Sonifier, Model 350, equipped with a microtip. The sonicates were combined and centrifuged at $30,000 \times g$ for 10 minutes. The supernatant was kept frozen at $-70°$ C. until use.

Enzyme activity was determined by assaying for 5-HETE formation by first incubating 0.2 ml of the supernatant obtained from the PMNL sonicate with the test compound, 1 mM $CaCl_2$, 2 mM ATP, and 1 mM GSH for 5 minutes at 37° C. The mixture is treated with 5 μM $^{14}C$-arachidonic acid and incubated at 37° C. an additional 10 minutes. The enzyme reaction was then stopped by the addition of 10 μl of 1M citric acid and 10 μl of an alcohol solution containing 20 mg/ml each of indomethacin and butylated hydroxyanisole (BHA). The reaction mixture was spotted (50 μl) on a silica gel plate (Baker TLC plate S1250-PA-19C) and subjected to TLC in a solvent system of ethyl acetate/2,2,4-trimethylpentane/glacial acetic acid/$H_2O$ (90:50:20:100).

The radioactivity of the arachidonic acid and its metabolites (5-HETE and $LTB_4$) was visualized from a developed x-ray film which had been exposed to the TLC plate 1–2 days. The amount of 5-HETE formed was quantitated by scraping the silica gel area corresponding to the spot on the x-ray film, and the radioactivity determined in a Isocap/300 liquid scintillation counter (Searle Analytic, Inc.).

The percent inhibition of the formation of 5-HETE was determined for each concentration of test compound tested as compared to a control experiment wherein no test compound was added. The concentration and percent inhibition values were plotted on semi log paper and the concentration in which formation of 5-HETE is inhibited by 50% ($IC_{50}$) was determined by interpolation. The results are summarized in Table I.

Fatty Acid Cyclooxygenase (FCO) Assay

Microsomes were prepared from 185 bags of human platelets (each bag containing the platelets from pint of blood prepared using differential centrifugation procedures). The platelets from approximately 60 bags were prepared at one time. Platelet-rich plasma (500 g) was centrifuged at $10,000 \times g$ for 20 minutes, and the platelet pellet was suspended in 100 ml of 0.1M potassium phosphate buffer, pH 8.0, with a Teflon glass homogenizer and sonicated for 5.0 minutes with a Bronson Sonifier (Model 350) in a rosette flask cooled in ice water. Disrupted platelets were centrifuged 15 minutes at $10,000 \times g$. The supernatant was centrifuged at $100,000 \times g$ for 90 minutes and the microsomal pellets were homogenized in 25 ml of 20% sucrose containing 1.0% Triton X-100 detergent. After 30 minutes at 4° C, the solubilized microsomes were centrifuged at $100,000 \times g$ for 60 minutes. The yellow supernatant was removed and stored at $-70°$ C.

The solubilized fatty acid cyclooxygenase was applied to a 440 ml electrofocusing column (LKB-8012) containing 1% phisolytes (Brinkman Instruments, Westburgh, N.Y.), pH 2-11, with the cathode at the top of the column. The enzyme was layered onto the column at the appropriate time so that its sucrose concentration was equal to that of the column gradient. This was accomplished by checking the gradient concentration periodically with a sucrose hand refractometer. Electrofocusing was carried out for 16 hours with an initial voltage of 400 V and a final voltage of 900–1,000 volts. Fractions were collected (20 ml) and assayed for $PGE_2$ formation. Active peak fractions were pooled add concentrated by ultrafiltration (XM 100A) to a volume of 3–5 ml.

Active fractions from electrofocusing were applied to a G-200 Sephadex column (2 cm $\times$ 46 cm) and eluted with 10 mM potassium phosphate buffer, pH 7.0, in 5 ml fractions. After assay, active fractions were pooled and concentrated to 1.0 ml by ultrafiltration (XM 100A), and kept frozen at $-70°$ C.

Enzyme activity was determined by assaying for $PGE_2$ formation by preincubating the enzyme with 10 mmol/l imidazole phosphate buffer, pH 8.0, 2 mmol/l epinephrine, 2 mmol/l methemoglobin, and the test compound (30 μg/ml) in a total volume of 0.2 ml for one minute at 37° C. After preincubation, 5 mmol/l $^{14}C$-arachidonic acid were added and the mixture was incubated an additional 0.5 minutes at 37° C. The enzyme reaction was stopped by the addition of 20 μl of indomethacin (2 mg/ml) in alcohol.

The reaction mixture was spotted (50 μl) on a silica gel (LQ6D) plate and subjected to TLC. The solvent system consisted of chloroform-methanol-glacial acetic acid (90:5:5, v/v/v) and the relative mobilities were $PGF_{2a}=0.235$, and $PGE_2 =0.47$. The silica gel on the plate was scraped in 1 cm sections, suspended in 5 ml of the scintillation fluid [5.88 g of 2,5-diphenyloxazole and 118 mg of 1,4-bis(5-phenyloxazol-2-yl)benzene]dissolved in 650 ml of toluene and 350 ml of Triton X-100) and the radioactivity was determined in an Isocap/300 liquid scintillation counter (Searle Analytic, Inc., Southfield, Mich.). Another 50 μl of the mixture was added to 10 ml of the Triton X-100 based scintillation fluid, and the radioactivity was determined so that the amount of radioactivity recovery from the TLC plate could be ascertained. $PGE_2$ formation for each test compound was determined as a percent of control experiments wherein no test compound was added. Data is expressed in Table I as the percent inhibition of formation of $PGE_2$ at a test compound concentration of 30 μg/ml.

Phospholipase $A_2$ ($PLA_2$) Assay

The assay buffer contained 10 mM Tris-HCl buffer, pH 8.0, 100 mM NaCl, 1 mM $CaCl_2$ and 1 mg/ml of bovine serum albumin. A toluene-ethanol (1:1 v/v) solution of phosphatidiylcholine, L-α-dipalmitoyl-(2-palmitoyl-1-$^{14}C$) obtained from New England Nuclear was evaporated to dryness in a flask under nitrogen and the assay buffer was added to give a substrate concentration of $9.0 \times 10^{-5}$M (specific activity $=27.7$ mCi/mmol). The mixture was sonicated for 5 minutes in a Bransonic 220 Sonication Bath. Pancreatic phospholipase $A_2$ (specific activity $=600$ units/mg) was diluted with the assay buffer to give an enzyme concentration of 0.1 mg/ml. To 0.1 ml of this enzyme solution, 30 μg/ml of test compound were added and the mixture was incubated for 15 minutes at 37° C. To initiate the enzyme reaction, 0.1 ml of the mixture containing the substrate was added to the enzyme solution and the reaction mixture was further incubated for 30 minutes at 37° C. The reaction was then terminated by the addition of 20 μl of 1M citric acid.

Fifty μl of the mixture was added to 10 ml of scintillation fluid [5.88 g of 2,5-diphenyl-oxazole and 118 mg of 1,4-bis(5-phenyloxazol-2-yl)benzene] dissolved in 650 ml of toluene and 350 ml of Triton X-100) and the radioactivity was determined in an Isocap/300 liquid scintillation counter (Searle Analytic Inc., Southfield, Mich.). Another 50 μl of the mixture was applied directly onto the spotting area of a silica gel plate (LK6D, Whatman, Clifton, N.J.) and subjected to thin layer chromatography in a solvent system of ethyl acetate:acetic acid:2,2,4-trimethylpentane:$H_2O$ (90:20:50:100, v/v/v). The silica gel on the plate was scraped in 1 cm sections, suspended in 5 ml of the Triton X-100 based scintillation fluid and the radioactivity was determined. Phosphatidylcholine remained at the origin while fatty acids migrated to a few centimeters (2–3 cm) below the solvent front. The percent of $^{14}C$-free fatty acid formed with the test compound added was calculated as compared to the amount formed in control experiments where no test compound was added. The data expressed in Table I are the percent inhibition of $^{14}C$-free fatty acid formation at a test compound concentration of 30 μg/ml.

TABLE 1

| Compound of Example No. | % Inhibition (30 μg/ml test compound) | | 5-LPO $IC_{50}$ (μg/ml) |
|---|---|---|---|
| | $PLA_2$ | FCO | |
| 1 | 77 | 77 | 0.4–1.0 |
| 2 | 82 | 75 | 0.15–0.6 |
| 3 | 41 | 67 | 0.15–0.4 |
| 4 | 0 | 52 | ~1 |
| 5 | 77 | 75 | 0.5–1.5 |
| 7 | 0 | 23 | NT* |
| 8 | 36 | 21 | NT |
| 9 | 0 | 46 | 0.8–6 |
| 10 | 26 | 25 | NT |
| 11 | 51 | 61 | 0.4 |

TABLE 1-continued

| Compound of Example No. | % Inhibition (30 μg/ml test compound) PLA₂ | FCO | 5-LPO IC₅₀ (μg/ml) |
|---|---|---|---|
| 12 | 72 | 16 | 5–12 |
| 13 | 50 | 47 | 8 |
| 14 | 72 | <5 | 6 |
| 15 | 88 | 32 | 0.08 |
| 16 | NT | 27 | 3 |
| 17 | NT | 12 | 3 |
| 18 | 44 | 20 | 10 |
| 19 | 76 | 14 | 1.5 |
| 21 | 0 | NT | 30 |

*not tested

DEVELOPING ADJUVANT-INDUCED ARTHRITIS TEST IN RATS

Compounds were tested for their ability to alter hind paw swelling and bone damage resulting from adjuvant-induced edema in rats. In order to quantitate the inhibition of hind paw swelling resulting from adjuvant-induced arthritis, two phases of inflammation have been defined: (1) the primary and secondary injected hind paw, and (2) the secondary uninjected hind paw, which generally begins developing about eleven days from the induction of inflammation in the injected paw. Reduction of the latter type of inflammation is an indication of immunosuppressive activity. Cf. Chang, *Arth. Rheum.*, 20, 1135–1141 (1977).

Adjuvant arthritis was induced in male Lewis-Wistar rats (200–210 grams) by a single subplantar injection into the right hind paw of 0.1 ml of a 0.5% suspension of heat-killed, lyophilized *Mycobacterium tuberculosis* (Calbiochem-Perrigen-C) in mineral oil (a modification of a method reported by Winter et al., *Arth. Rheum.*, 9, 394–397 (1966)). One group of 10 rats ("TB control") received only this treatment. Another group of 5 rats received no treatment (normal control). Each compound to be tested was suspended in carboxymethylcellulose (1%) and administered i.p. to rats (groups of 5 each) in daily doses of 50 mg/kg beginning on day one and continuing through the 28th day after the adjuvant injection (29 doses). Paw volumes were measured by mercury displacement using a Statham pressure transducer and digital voltmeter. Volumes of both the injected and the uninjected hind paws were measured on days 16, 18, 21, 23, 25, 28, and 30. X-ray photos were taken on day 30, after the animals were sacrificed. The paw volume measurements on the uninjected paw beginning with day 16 through day 30 were computer plotted for the TB controls, the normal controls, and the drug-treated animals, and the areas under the curves [(TB controls minus normal controls) and (treated animals minus normal controls)] were determined. The results are summarized in Table II.

Table II

Inhibition of Uninjected Paw Volume Inflammation Days 16 through 30

| Compound of Example No. | Dose mg./kg. I.P. x 29 | % Inhibition* |
|---|---|---|
| 1 | 50 | 56.0% |
| 7 | 50 | 37.6% |
| 10 | 50 | 100.0% |
| 11 | 50 | 69.0% |
| 12 | 50 | 40.6% |
| 17 | 50 | 28.4% |

*% inhibition is the difference of the areas under the curves (AUC) of the mean uninjected paw volumes plotted for days 16, 18, 21, 23, 25, 28 and 30 according to the following formula:

$$\% \text{ inhibition} = \left[ 1 - \frac{\text{(Drug treated AUC)} - \text{(normal control AUC)}}{\text{(TB control AUC)} - \text{(normal control AUC)}} \right] \times 100$$

Gross observation of X-ray photos taken of uninjected paws showed considerable inhibition of bone damage in the treated animals as compared to the TB control group. A substantial inhibition of bone damage was also seen in a comparison of the injected paws.

The compounds of this invention have also been demonstrated to be active in the carrageenan rat paw edema assay, the collagen type II arthritis assay, and the delayed-type hypersensitivity assay.

The compounds of this invention may be administered by various routes including the oral, rectal, transdermal, subcutaneous, intravenous, intramuscular, or intranasal routes. The compounds are usually employed in the form of pharmaceutical compositions. Such compositions are prepared in a manner well known in the pharmaceutical art and comprise an effective amount of at least one active compound of the invention. Accordingly, the invention includes a pharmaceutical composition comprising as active ingredient a compound of Formula I associated with a pharmaceutically acceptable carrier.

In making the compositions of the present invention, the active ingredient will usually be mixed with a carrier, or diluted by a carrier, or enclosed within a carrie which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may, as is well known in the art, be formulated so as to provide quick, sustained or delayed release of the active ingredient after administration to the patient.

The compositions usually contain as active ingredient from about 1% to about 95% by weight of a compound of the invention and are preferably formulated in a unit dosage form, each dosage containing from about 0.5 to about 500 mg, more usually about 1 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The active compounds are effective over a wide dosage range and typical dosages per day will normally fall within the range of about 0.020 to about 300 mg/kg of body weight. In the treatment of adult humans, a range of from about 0.020 to about 50 mg/kg, in single or divided doses, is preferred. However, it will be understood that the amount of the compound actually administered will be determined by a physician in the light of the relevant circumstances including the condition to be treated, the choice of compound to be administered, the chosen route of administration, the age, weight, and response of the individual patient, and the severity of the patient's symptoms, and therefore the above dosage ranges are not intended to limit the scope of the invention in any way.

The following formulation examples may employ as active ingredients any of the pharmaceutical compounds of the invention. The examples are illustrative only and are not intended to limit the scope of the invention in any way.

EXAMPLE 22

Hard gelatin capsules are prepared using the following ingredients:

| | Quantity (mg/capsule) |
|---|---|
| 5-hydroxy-4-[12-(1-naphthalenyl-oxy)dodecyl]-2(5H)—furanone | 250 |
| Starch dried | 200 |
| Magnesium stearate | 10 |

The above ingredients are mixed and filled into hard gelatin capsules in 460 mg quantities.

EXAMPLE 23

A table formula is prepared using the ingredients below:

| | Quantity (mg/tablet) |
|---|---|
| (Z,Z)-4-(7,10-hexadecadienyl)-5-hydroxy-2(5H)—furanone | 250 |
| Cellulose, microcrystalline | 400 |
| Silicon dioxide, fumed | 10 |
| Stearic acid | 5 |

The components are blended and compressed to form tablets each weighing 665 mg.

EXAMPLE 24

An aerosol solution is prepared containing the following components:

| | Weight % |
|---|---|
| 5-hydroxy-4-(4,8,12-trimethyl-3,7,11-tridecatrienyl)-2(5H)—furanone | 0.25 |
| Ethanol | 29.75 |

| | Weight % |
|---|---|
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted with the remaining amount of propellant. The valve units are then fitted to the container.

EXAMPLE 25

Tablets each containing 60 mg of active ingredient are made up as follows:

| | |
|---|---|
| 4-(18-eicosenyl)-5-hydroxy-2(5H)—furanone | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a table machine to yield tablets each weighing 150 mg.

EXAMPLE 26

Capsules each containing 80 mg of medicament are made as follows:

| | |
|---|---|
| (Z,Z)-4-(7,10-hexadecadienyl)-5-hydroxy-2(5H)—furanone | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

EXAMPLE 27

Suppositories each containing 225 mg of active ingredient are made as follows:

| | |
|---|---|
| 4-(7,14-hexadecadienyl)-5-hydroxy-2(5H)—furanone | 225 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 28

Suspensions each containing 50 mg of medicament per 5 ml dose are made as follows:

| | |
|---|---|
| 5-hydroxy-4-nonyl-2(5H)—furanone | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethylcellulose and syrup to form a smooth paste. The benzoic acid solution, flavor and color are diluted with some of the water and added, with stirring. Sufficient water is then added to produce the required volume.

EXAMPLE 29

A topical ointment containing 100 mg of active ingredient per gram of ointment is made by blending the following ingredients:

| | mg/gram ointment |
|---|---|
| 5-hydroxy-4-(4,8,12-trimethyl-3,7,11-tridecatrienyl)-2(5H)—furanone | 100 |
| Polyethylene glycol 300 (N.F.) | 600 |
| Polyethylene glycol 4000 (U.S.P.) | 300 |

We claim:

1. A compound of the formula

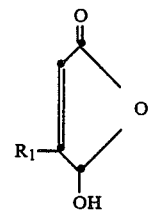

wherein $R_1$ is a $C_{16}-C_{20}$ straight or branched chain hydrocarbyl group optionally containing a total of 1–6 double and/or triple bonds and optionally containing an aldehyde or hydroxymethyl group, or R-alk- where alk is a $C_2-C_{12}$ straight or branched chain alkylidene group optionally containing 1 or 2 double or triple bonds and R is napthalenyloxy or benzylphenoxy.

2. A compound of claim 1 wherein $R_1$ is an alkadienyl or alkatrienyl group.

3. The compound of claim 2 which is (Z,Z)-4-(7,10-hexadecadienyl)-5-hydroxy-2(5H)-furanone.

4. The compound of claim 2 which is 5-hydroxy-4-(4,8,12-trimethyl-3,7,11-tridecatrienyl)-2(5H)-furanone.

5. A compound of claim 1 which $R_1$ is R-alk-and R is naphthalenyloxy.

6. The compound of claim 5 which is 5-hydroxy-4-[4-(2-naphthalenyloxy)butyl]-2(5H)-furanone.

7. A pharmaceutical formulation which comprises a compound of claim 1 in association with a pharmaceutically-acceptable carrier, excipient, or diluent therefor.

8. A formulation according to claim 7 employing a compound wherein $R_1$ is a hydrocarbyl group of 10–20 carbon atoms containing 2–4 double bonds.

9. A formulation according to claim 8 employing a compound wherein $R_1$ is a hydrocarbyl group of 12–16 carbon atoms.

10. A formulation according to claim 9 employing (Z,Z)-4-(7,10-hexadecadienyl)-5-hydroxy-2(5H)furanone.

11. A formulation according to claim 9 employing 5-hydroxy-4-(4,8,12-trimethyl-3,7,11-tridecatrienyl)-2(5H)-furanone.

12. A formulation according to claim 7 employing a compound wherein $R_1$ is R-alk- and R is naphthalenyloxy.

13. A formulation according to claim 12 employing 5-hydroxy-4-[4-(2-naphthalenyloxy)butyl]-2(5H)furanone.

* * * * *